(12) United States Patent
Bublitz et al.

(10) Patent No.: US 8,632,181 B2
(45) Date of Patent: Jan. 21, 2014

(54) SS OCT INTERFEROMETRY FOR MEASURING A SAMPLE

(75) Inventors: Daniel Bublitz, Jena (DE); Gerhard Krampert, Jena (DE); Martin Hacker, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 349 days.

(21) Appl. No.: 12/997,804

(22) PCT Filed: Jun. 12, 2009

(86) PCT No.: PCT/EP2009/004263
§ 371 (c)(1),
(2), (4) Date: Mar. 21, 2011

(87) PCT Pub. No.: WO2009/149953
PCT Pub. Date: Dec. 17, 2009

(65) Prior Publication Data
US 2011/0157552 A1    Jun. 30, 2011

(30) Foreign Application Priority Data

Jun. 13, 2008 (DE) .......................... 10 2008 028 312

(51) Int. Cl.
*A61B 3/14* (2006.01)
*A61B 3/00* (2006.01)
*A61B 3/113* (2006.01)

(52) U.S. Cl.
CPC .................................. *A61B 3/113* (2013.01)
USPC ........................... 351/209; 351/210; 351/246

(58) Field of Classification Search
USPC .......... 351/209, 246, 205, 206, 208, 210, 221
See application file for complete search history.

(56) References Cited

U.S. PATENT DOCUMENTS

| | | | |
|---|---|---|---|
| 4,938,584 A | 7/1990 | Suematsu et al. |
| 5,347,327 A | 9/1994 | Sekine et al. |
| 5,638,176 A | 6/1997 | Hobbs et al. |
| 6,198,540 B1 | 3/2001 | Ueda et al. |
| 6,325,512 B1 | 12/2001 | Wei |

(Continued)

FOREIGN PATENT DOCUMENTS

| | | |
|---|---|---|
| DE | 31 34 574 A1 | 3/1983 |
| DE | 32 01 801 A1 | 9/1983 |

(Continued)

OTHER PUBLICATIONS

Chang-Hasnain, Connie J., "Tunable VCSEL," *IEEE Journal on Selected Tiopics in Quantum Electronics*, vol. 6, No. 6, Nov./Dec. 2000 (pp. 978-987).

(Continued)

*Primary Examiner* — Jack Dinh
(74) *Attorney, Agent, or Firm* — Patterson Thuente Pedersen, P.A.

(57) ABSTRACT

An SS OCT interferometry device for measuring a sample, in particular from an eye. The device interferometrically generates a measuring signal and from the signal a depth-resolved contrast signal of the sample by spectral tuning of the central wavelength of the measurement radiation of a measuring signal, and has a control unit for this purpose. The device includes a sample motion detector, which provides a motion signal indicating movement of or in the sample, the control unit uses the motion signal to correct the measuring signal with respect to measuring errors that are caused by a movement of or in the sample before or during the generation of the depth-resolved contrast signal.

27 Claims, 3 Drawing Sheets

(56) References Cited

U.S. PATENT DOCUMENTS

| | | |
|---|---|---|
| 6,726,325 B2 | 4/2004 | Xie et al. |
| 6,736,508 B2 | 5/2004 | Xie et al. |
| 6,806,963 B1 | 10/2004 | Waelti et al. |
| 2002/0015041 A1 | 2/2002 | Naegle et al. |
| 2002/0154141 A1 | 10/2002 | Forman |
| 2004/0239943 A1 | 12/2004 | Izatt et al. |
| 2005/0140981 A1 | 6/2005 | Waelti |
| 2006/0109477 A1 | 5/2006 | Zhou et al. |
| 2007/0076217 A1 | 4/2007 | Baker et al. |
| 2008/0285043 A1 | 11/2008 | Fercher et al. |

FOREIGN PATENT DOCUMENTS

| | | |
|---|---|---|
| DE | 35 27 245 A1 | 2/1987 |
| EP | 0 348 057 B1 | 4/1993 |
| EP | 0 509 903 B1 | 9/1996 |
| WO | WO 01/38820 A1 | 5/2001 |
| WO | WO 2007/065670 A2 | 6/2007 |

OTHER PUBLICATIONS

Maguluri, Gopi, et al., "Three dimensional tracking for volumetric spectral-domain optical coherence tomography," *Optics Express*, vol. 15, No. 25, Dec. 10, 2007 (pp. 16808-16817).

Choma, Michael A., et al., "Sensitivity advantage of swept source and Fourier domain optical coherence tomography," *Optics Express*, vol. 11, No. 18, Sep. 8, 2003 (pp. 2183-2189).

Huang, David, et al., "Optical Coherence Tomography," *Science*, vol. 254, Nov. 22, 1991 (pp. 1178-1181).

Zhuang, Zhizhong, et al., "Polarization controller using nematic liquid crystals," *Optics Letters*, vol. 24, No. 10, May 15, 1999 (pp. 694-696).

Lexer, F., et al., "Wave-length-tuning interferometry of intraocular distances," *Applied Optics*, vol. 36, No. 25, Sep. 1, 1997 (pp. 6548-6553).

Schmetterer, Leopold F., et al., "Topical measurement of fundus pulsations," *Optical Engineering*, vol. 34, No. 3, Mar. 1995, (pp. 711-716).

Huber, R., "Fourier Domain Mode Locking (FDML): A new laser operating regime and applications for optical coherence tomography," *Optics Express*, vol. 14, No. 8, Apr. 17, 2006 (pp. 3225-3237).

SS OCT INTERFEROMETRY FOR MEASURING A SAMPLE

PRIORITY CLAIM

The present application is a National Phase entry of PCT Application No. PCT/EP2009/004263, filed Jun. 12, 2009, which claims priority from German Application Number 102008028312.6, filed Jun. 13, 2008, the disclosures of which are hereby incorporated by reference herein in their entirety.

FIELD OF THE INVENTION

The invention relates to an SS-OCT interferometer apparatus for measuring a sample, in particular an eye, wherein the apparatus interferometrically generates, by means of spectral tuning of the central wavelength of a measurement radiation, a measurement signal and, from this, a depth-resolved contrast signal of the sample and has a control device for this.

The invention further relates to an SS-OCT method for measuring a sample, in particular an eye, wherein, by means of spectral tuning of the central wavelength of a measurement radiation, a measurement signal and, from this, a depth-resolved contrast signal of the sample is interferometrically generated.

BACKGROUND

To measure transparent or partially transparent samples, for example of the human eye, short-coherence interferometers which operate by means of optical coherence tomography (hereinafter: OCT) are known, for example from WO 2007/065670 A1. They serve to detect the location and size of scattering centres within a sample, such as for example miniaturized optical components or biological tissue, e.g. the human eye. For an overview of the corresponding literature on OCT, reference may be made to US 2006/0109477 A1. This patent publication, which partly goes back to one of the inventors of the invention relevant here, also describes the basic principles of OCT.

The principle of OCT comprises both embodiments in which irradiation and radiation detection occur by scanning at different locations across the direction of incidence of the radiation and embodiments, simplified compared with these, in which the irradiation and radiation detection is carried out only along an axis that remains unaltered and axial (i.e. 1-dimensional) scattering profiles are thus generated. The latter embodiment corresponds, as far as the image production is concerned, to a so-called A-scan of ultrasound image production; it is also called optical coherence domain reflectometry (OCDR). When OCT is mentioned here, it is to be understood to mean both scanning and OCDR systems.

Essentially three variants are known for OCT: in time domain OCT, the eye is illuminated by a short-coherent radiation, and a Michelson interferometer ensures that radiation scattered back from the eye can interfere with radiation which has passed through a reference beam path. This principle, already described at a relatively early stage in Huang, et al., Science 254: 1178-1181, 1991, can achieve a depth-resolved image of the sample if the length of the reference beam path is adjusted, whereby a window corresponding to the coherence length of the radiation used is adjusted in the sample. The size of this window defines the maximum achievable depth resolution. For a good depth resolution, radiation sources with the shortest possible coherence, i.e. spectrally wide, are thus necessary. Because of the measurement method, only a fraction of the radiation reflected back, i.e. that scattered back from the measurement depth of the sample, which corresponds to the length of the reference beam path, is detected at any time. In known structures, therefore, over 99% of the photons scattered back from the sample are not actually detected for the measurement.

A higher yield is obtained with another OCT variant, frequency domain OCT. Here, the length of the reference beam path is no longer altered; instead, the radiation brought to interference is detected spectrally resolved. The depth information of the sample, i.e. the depth-resolved contrast signal, is calculated from the spectrally resolved signal. As a mechanism for adjusting the path length of the reference beam path is no longer necessary, the FD-OCT technique is capable of measuring simultaneously at all depths of the sample. The thereby achieved higher yield of the radiation scattered back achieves a sensitivity up to 20 dB higher for the same measurement time. A disadvantage of FD-OCT systems is the maximum measurement range size, which is limited by the spectrometer resolution, and the reduction in sensitivity which increases with the measurement depth. The required structure is also much more expensive.

The SS-OCT variant, in which the spectral resolution of the interference signal with a spectrometer is dispensed with and, instead, the illumination source is spectrally tuned, requires somewhat less additional structural outlay. This method is more sensitive than TD-OCT because of the higher photon yield, as M. Choma et al. explain in "Sensitivity advantage of swept source and Fourier domain optical coherence tomography," Opt. Express 11, 2183-2189 (2003). In the case of SS-OCT, too, the maximum resolution corresponds to the tunable wavelength range of the radiation source, and the measurement range is predetermined by the coherence length of the radiation used.

In all OCT variants, the measurement range and the measurement resolution are thus linked in a certain way. To rectify the limitation imposed by this, WO 2007/065670 A1 skillfully describes combining several interferometer arrangements which are each assembled from their own reference beam path as well as an associated sample beam path. By different matching of these several interferometer arrangements which, although combined in one apparatus, are independent, measurements can be taken simultaneously at different points in the eye and thus the measurement range can be enlarged. The document further describes different approaches for differentiating the radiations in the combined interferometers, for example in respect of the polarization of the radiation or the wavelength. Such a differentiation is also described in WO 2001/038820 A1 which, however, is concerned only with TD-OCT, thus requires moving elements for adjusting the length of the reference beam path. The principle of using several reference beam paths of different lengths can also be found in US 2005/0140981, or in U.S. Pat. No. 6,198,540, which each relate to TD-OCT for enlarging the measurement range and use several, individually adapted reference beam paths of different lengths.

SUMMARY OF THE INVENTION

If it is not desired to incur the outlay caused by several, individually matched reference beam paths, there remains, in particular with SS-OCT, the problem that as wide as possible a spectral tuning range has to be passed through, with as narrow-band as possible a radiation source. At the same time, the passage should be as fast as possible in order to keep the measurement time short. The sources that satisfy these requirements in the field of eye measurement and which e.g.

allow the eye length to be determined with sufficient precision are very laborious and expensive. More favourable tunable laser beam sources can for example be tuned thermally or via the current, but have very limited tuning ranges (e.g. 1-2 nm) and unfavourable spectral characteristics. Also, because the speed of tuning (0.3-36 nm/s) is too slow, they require too-long tuning times of up to 10 seconds, during which changes in eye length due to pulsations represent a problem. This problem currently limits use on the human eye with technically comparatively inexpensive sources to a tuning range below 0.2 nm, as pulsations, for example pulsations of the eye length due to blood pressure, cause a change of roughly 0.3 μm in distance between cornea and retina within half a second and thus make longer tuning periods impossible.

The invention is therefore based on the object of developing an SS-OCT interferometer apparatus or an SS-OCT method of the named type such that measurements in the field of eye length with sufficient resolution are possible.

This object is achieved by an SS-OCT interferometer apparatus of the type named at the beginning, wherein the apparatus comprises a sample-motion detector which provides a motion signal that indicates movements of the sample or in the sample, and that, before or during the generation of the depth-resolved contrast signal, the control device corrects, by means of the motion signal, the measurement signal in respect of measurement errors which are caused by movements of the sample or in the sample that occurred during the tuning.

By sample movement is also meant here a change in the position of the sample, with the result that the sample-motion detector can also be a position-change detector.

The object is further achieved by an SS-OCT method of the type named at the beginning, wherein movements of the sample or in the sample are detected and a motion signal indicating these is generated and, before or during the generation of the depth-resolved contrast signal, the measurement signal is corrected, by means of the motion signal, in respect of measurement errors which are caused by movements of the sample occurring during the tuning.

The invention takes as its starting point the approach pursued in the state of the art of keeping the measurement time so short that movements of the sample, in particular pulsations of the eye, are negligible and instead takes measures to correct measurement errors which are caused by movements of the sample, by using for the apparatus according to the invention a sample-motion detector which provides a motion signal indicating movements of the sample or in the sample or, in the case of the apparatus according to the invention, a corresponding motion detection.

The motion signal obtained in this way is then preferably not used simply to correct the depth-resolved contrast signal, such as would be possible for example with a simple eye-tracking system, but the interferometrically obtained measurement signal which results from the tuning of the measurement radiation source is correspondingly corrected with the motion signal. The correction thus preferably starts before a transformation that converts the interferometric measurement signal into a depth-resolved contrast signal, e.g. before a corresponding Fourier transform. The start of the correction at this point in the procedure has the advantage that a very simple correction signal can be used and at the same time a fully complete error correction is obtained.

The simplicity of the correction signal is inter alia also that a tracking of moving sample parts during the motion detection can be dispensed with. In an embodiment, it suffices to use a motion signal which indicates the contrast in a reference section of the sample that is at a fixed distance from the apparatus. The term "fixed distance" refers to the optical path length as far as detection/the detector. This makes it possible to operate with a spatially fixed sample-motion detection or a sample-motion detector which manages without tracking. The correction signal then indicates exclusively the change in contrast in the reference section, which is then used to correct the measurement signal.

A particularly marked change in contrast is obtained if the reference section in the sample contains a surface of the sample or a boundary surface of the sample, as a small movement of the sample already then leads to a marked change in signal.

The motion signal is particularly suitable to simply correct the measurement signal if it is of the same type, thus is also an interference signal. It is therefore particularly preferred if the sample-motion detection is interferometric in an analogous manner, like the generation of the measurement signal. It is therefore preferred that the sample-motion detection is interferometric by means of correction radiation fixed spectrally in the central wavelength, as changes in the correction signal can then very easily be used to correct the measurement signal.

The interferometric generation of the measurement signal and the correction signal can in principle use any suitable interferometer structure. The variable to be measured then results from the speed of phase change of the measurement signal. The detection of the phase change of the correction signal then allows a correction based on movement of the sample. This is true in particular for embodiments which operate with a fixed reference in the form of a stationary reference object, e.g. for an interferometer with a reference beam path at the end of which there is a reflector which does not automatically move with the sample.

The use of an interferometrically produced correction signal is, however, also possible with embodiments which use a point on the sample itself as reference. Fluctuations in distances within the sample, such as can occur e.g. during eye-length measurements, are then corrected. In the case of an eye-length measurement, e.g. the reflexes of cornea front surface and fundus of the eye are then coherently superimposed, in both the measurement and correction channels. The temporal phase change of the measurement signal (phase change rate) essentially originates from the tuning of the source and is directly proportional to the speed of tuning and the eye length. If the eye length changes during the measurement, an additional (ancillary) phase change results. In the correction signal the central wavelength of which is not tuned, the phase change due to the change in eye length is measured separately and the measurement signal can thus be corrected, with the result that the average eye length can be calculated from the corrected signal. Measures must be taken here in order to achieve the interference capability. The interference capability can be achieved e.g. by using light sources of sufficient coherence length or, if the coherence length of the light source is insufficient, by using known pre- or post-interferometers (e.g. DE 3201801C2).

A Michelson arrangement is particularly preferred because of the simple structure, with the result that the apparatus has a sample beam path, illuminates the sample through a part of the measurement radiation emitted from the measurement radiation source and has a detection beam path, receives, superimposed, the measurement radiation reflected or scattered back from the sample as sample measurement radiation and detects it by means of a detector device, and the sample-motion detector comprises a correction radiation source which emits the correction radiation, wherein a part of the correction radiation is coupled into the sample beam path and illuminates the sample, and the detection beam path receives correction radiation reflected or scattered back from the sample as sample correction radiation and detects it by means of the detector device separately from the measurement radiation, and the control device generates the correction signal from signals of the detection of the correction radiation. To detect movement over the widest possible ranges, a correction radiation source which emits monomodal laser radiation is advantageous.

It applies analogously to the method that the sample is illuminated by a part of the measurement radiation, and measurement radiation reflected or scattered back from the sample is detected, wherein part of the correction radiation also illuminates the sample, and correction radiation reflected or scattered back from the sample is detected independently and the correction signal is generated from it.

This concept can be extended to include a reference beam path through which part of the measurement radiation emitted from the measurement radiation source passes as reference measurement radiation. The detection beam path then superimposes the sample measurement radiation with the reference measurement radiation. Analogously, part of the correction radiation also passes as reference correction radiation through the reference beam path and is superimposed with the reference correction radiation in the detection beam path.

The sample is thus illuminated by both the measurement radiation and correction radiation, measurement and correction radiation scattered back or reflected at the sample is optionally superimposed with measurement and correction radiation which has passed through a reference beam path. The detector device always records a corresponding interference signal, wherein sample measurement radiation and correction radiation are detected independently, i.e. separately. The measurement signal is produced from the detection of the sample measurement radiation, the correction signal from the detection of the sample correction radiation.

For depth resolution, the wavelength of the measurement radiation is tuned, but the central wavelength of the correction radiation remains constant, with the result that the interference originates from a specific volume that was unchanged vis-à-vis the OCT during the measurement and which corresponds to the reference section. Of course, its position in or at the sample will change because of movements of the sample, such as described e.g. in DE 3134574 C2 where a person skilled in the art can find them. This document is therefore explicitly incorporated by reference here.

For the separation of measurement radiation and correction radiation, both a spectral and a polarization separation are possible. Further alternatives are a geometric separation (e.g. pupil separation), multiplex operation (e.g. alternating activation of the sources) and modulation and filtering at different frequencies.

Studies have shown that eye movements, in particular eye pulsations, substantially influence the phase function of the recorded signal. It is therefore preferable to split the measurement and the correction signal in respect of amplitude function and phase function and to correct the phase function of the measurement signal through reference to the phase function of the correction signal, for example by removing the phase function of the correction signal from that of the measurement signal. This can preferably take place when the wavelengths of measurement radiation and correction radiation lie close together. The following then applies to the corrected phase function $\Phi'_M$ of the measurement radiation $\Phi'_M = \Phi_M - \Delta\Phi_K$, wherein $\Phi_M$ is the phase of the measurement radiation and $\Delta\Phi_K$ a detected phase change in the correction signal.

A consideration independent of this approximation gives the following relationship $$\Phi'_M = \Phi_M - \Delta\Phi_K \frac{\lambda_K \cdot n(\lambda_M)}{\lambda_M \cdot n(\lambda_K)},$$

wherein $\lambda_K$ denotes the wavelength of the correction radiation, $\lambda_M$ the wavelength of the measurement radiation, and $n(\lambda)$ the wavelength-dependent refractive index.

The separation of the signals into amplitude and phase functions can take place particularly easily by means of a heterodyne detection. Alternatively, a quadrature component detection can also be used, such as is described for example in US 2004/0239943.

For a heterodyne detection, a modulation of the measurement radiation and the correction radiation takes place in each case around its central wavelength. This modulation can be applied e.g. to a supply current of the measurement and correction radiation source, preferably with a stability of the supply current generation better than 0.8 µA, if an ophthalmological eye-length measurement is to take place. A stability of the power supply better than 0.8 µA corresponds to a coherence length of 100 mm. The amplitude of the modulation of the wavelength, in contrast, is only about $\lambda/2 L_{eye} = \delta\lambda/\lambda$. If $\lambda=850$ nm and $L_{eye}=24$ mm, it follows that $\delta\lambda > 0.015$ nm. If there is a shift of the wavelength as a function of the current with the described example source of 0.21 nm/mA, it corresponds to a minimum current modulation of 70 µA.

In addition to the correction of the phase function, the amplitude function of the measurement signal can be resealed before the generation of the contrast signal. The amplitude function as a function of time is determined from the intensity of the interferences during the modulation. The amplitude correction means that the amplitude is always corrected at time t to a constant value, e.g. the initial value $A(t_0)$. This is a prerequisite if the signal is then to be evaluated with a Fourier transform.

The procedure according to the invention makes it possible to use radiation sources for the SS-OCT that are clearly more cost-advantageous and were not previously usable because of their speeds of tuning. Examples of such radiation sources are: External Cavity Diode Laser, Distributed Feedback Laser, Distributed Bragg Reflector Laser, Vertical Cavity Surface Emitting Laser, Vertical External Cavity Emitting Laser.

Insofar as method steps are described above or below, the mentioned control device ensures that the described apparatus carries out the corresponding method. Method features named here are thus also features of the control device in the mode of operation of the control device. Of course, operating properties of the control device are also to be understood as method features of the corresponding method.

It is understood that the features named above and still to be explained below can be used not only in the given combinations, but also in other combinations or alone, without departing from the framework of the present invention.

BRIEF DESCRIPTION OF THE DRAWINGS

The invention is explained in further detail below by way of example using the attached drawings which also disclose features essential to the invention. There are shown in.

DETAILED DESCRIPTION

Figure 1A:
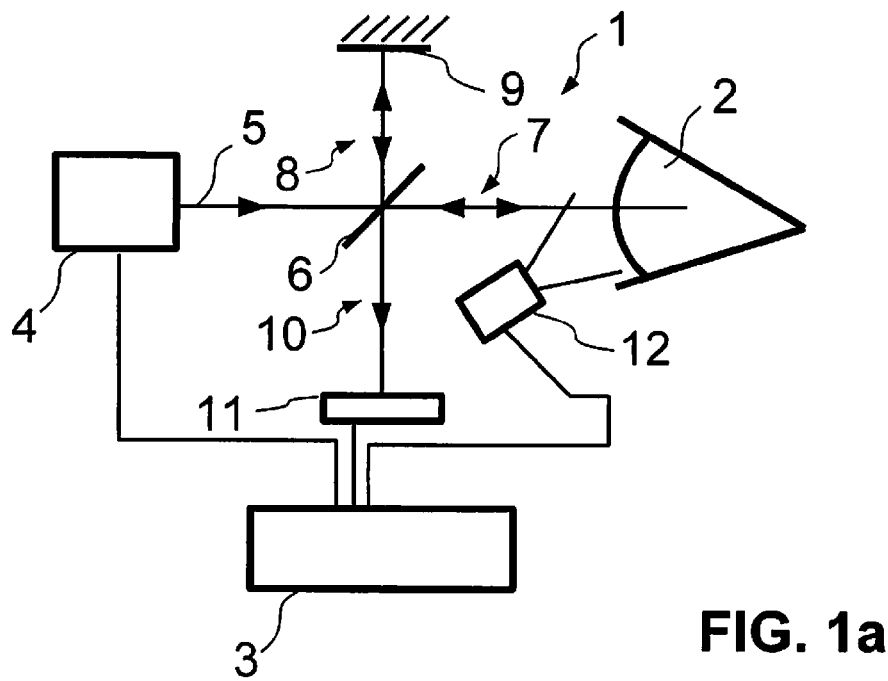
FIG. 1a is a schematic representation of an OCT for eye-length measurement, wherein the OCT has an independent reference beam path.

An OCT 1 operating according to the principle of a Michelson interferometer which carries out measurements on an eye 2 of a patient is represented in FIG. 1a. However, this use of the OCT 1 is exemplary; other measurement tasks can also be carried out with it, for example transparent waveguide structures or other structures relevant in semi-conductor engineering terms can be measured. The measurement of other biological tissue is also possible.

The operation of the OCT 1 is controlled by a control device 3 which is connected to the corresponding components of the OCT 1, controls these, reads out measurement values supplied by these and from this provides the desired imaging information on the sample, in this case the eye 2, and (in a manner not represented) displays it or transmits corresponding data.

The OCT 1 has a measurement laser 4 which is formed as a VCSEL (Vertical Cavity Surface Emitting Laser). It emits spectrally narrow-band radiation, which at a wavelength of roughly 850 nm leads to a coherence length of typically 100 mm (spectral width of 0.007 nm). State of the art are VCSELs with e.g. 30 MHz line width (Avalon Photonics), i.e. achievable scanning depths that are substantially larger than necessary for length measurements on the whole eye. The relationship between scanning depth and line width is described inter alia by $$\Delta z = \frac{2\ln 2}{\pi} \frac{\lambda^2}{\delta\lambda}$$

(cf. F. Lexer et al., Appl. Optics 36, p. 6549 "Wavelength-tuning interferometry of intraocular lenses").

The central wavelength of the measurement radiation 5 emitted from the measurement laser 4 can be tuned spectrally by altering the operating temperature or suitably altering the external cavity. Such a laser is described for example in the publication Chang-Hasnain, C. J., "Tunable VCSEL", IEEE Journal of selected topics in Quantum Electronics, 2000, Volume 6, pages 978-987. The measurement radiation 5 strikes a beam splitter 6 which allows part of the measurement radiation to pass into a sample beam path 7 leading to the eye 2. Another part of the measurement radiation 5 is diverted by the beam splitter 6 into a reference beam path 8, at the end of which there is a mirror 9.

The sample 2 scatters back or reflects in different depth ranges the incident part of the measurement radiation 5, with the result that radiation reflected or scattered back at the sample 2 travels back to the beam splitter 6 again as a sample measurement radiation in the sample beam path 6 against the direction of incidence of the measurement radiation 5. This is symbolized by a double arrow for the radiation in the sample beam path 7.

The process is similar in the reference beam path at the end of which the mirror 9 reflects the measurement radiation, which is why a corresponding double arrow is also included for the radiation in the reference beam path 8. The part of the measurement radiation 5 that has passed through the reference radiation path 8 is at least partially transmitted at the beam splitter 6 and enters a detection beam path 10, where it is superimposed with the sample measurement radiation which is also introduced into the detection beam path 10 by the beam splitter 6. The parts of the measurement radiation superimposed in this way (the part passing through the reference beam path as well as the part reflected or scattered back from the eye 2) interfere with each other at the detector 11 which records a corresponding interference signal and relays it to the control apparatus 3.

Figure 1B:
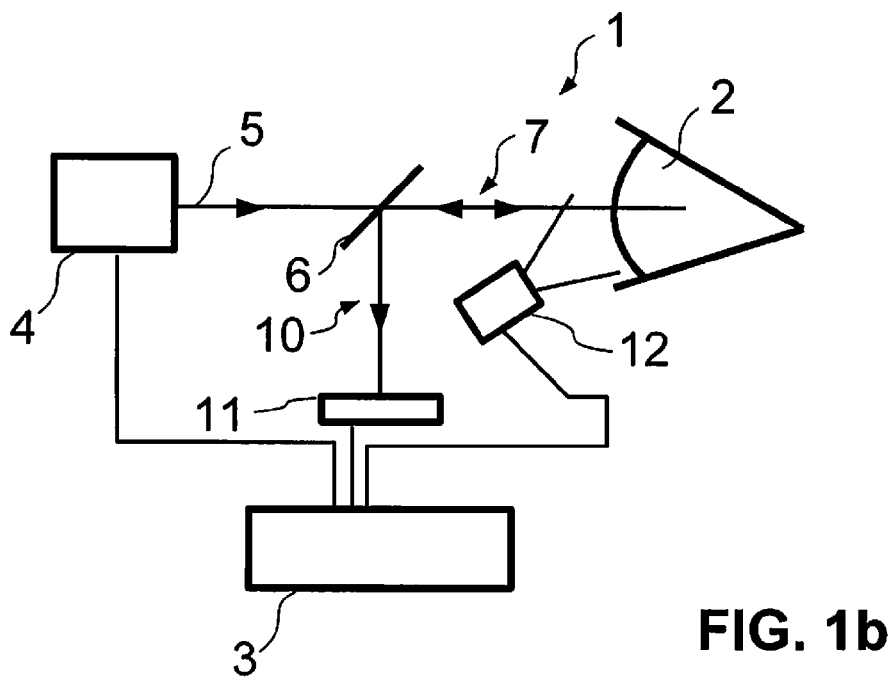
FIG. 1b is an OCT similar to that of FIG. 1a, wherein the OCT of FIG. 1b does not have a reference beam path, but causes radiation reflected or scattered back from different depth areas of the eye to interfere with each other.

FIG. 1b shows a variant of the OCT 1 of FIG. 1a which operates without a reference beam path 8. Here, parts of the measurement radiation 5 which have been reflected or scattered back from different areas of the sample interfere in the detection beam path 10, wherein the maximum distance between the areas depends on the coherence length of the measurement radiation 5. With SS-OCT, the distances between the structures in the sample may only be smaller than the coherence length of the sources used (otherwise the radiation does not interfere and the method does not function). However, much more important is that the distances between the structures must also be greater than the depth resolution of the measurement method which results essentially from the width of the maximum tuning range. If the source described by way of example can be tuned by at most 3 nm at 850 nm, the structures are at a minimum distance of 240/2=120 μm and a maximum distance of 100/2=50 mm.

The structure of FIG. 1b has the advantage of a better utilization of the measurement radiation 5 used, as an additional selection of the interfering radiation is not, as in the structure of FIG. 1a, carried out by the wavelength of the reference beam path 8. Apart from this, the variants of FIGS. 1a and 1b do not differ further, with regard to the invention described here, with the result that the previous or following description is equally valid for both variants.

In order to measure a larger area in the eye, the central wavelength of the measurement radiation 5 is tuned by suitable control of the measurement laser 4. The interference signal recorded by the detector 11 is then present as a wavelength-dependent measurement signal and the control apparatus 3 can generate a depth-resolved contrast signal from it, by means of Fourier transform, via the contrast in the eye 2 along the direction of incidence of the measurement radiation 5, such as is known for SS-OCT. Evaluation algorithms customary in SS-OCT can be used here.

However, a change in length or movement of the eye, due to e.g. pulse beat, breathing or microsaccades, leads to a change in the measurement signal which is a motion artefact and distorts the measurement signal and thus the contrast signal generated from it. Because of the tuning period required by the VCSEL in the measurement laser 4, such distortions cannot be ruled out when measuring the eye length, as the measurement duration can lie in the range of several seconds.

The OCT 1 of FIG. 1a or 1b therefore has a sample-motion detector 12 which can be designed in the structure of FIGS. 1a and 1b for example as a known eye-tracker, such as is used in eye surgery, and which records movements of the eye, for example of the cornea front surface or the eye lens interface.

The sample-motion detector 12 delivers a corresponding motion signal to the control device 3 which indicates this information on movements of the eye 2 or movements of structures in the eye 2. The sample-motion detector can, depending on the embodiment, deliver a specific motion signal which gives the direction and extent of the movement of the monitored structure. However, in a variant simplified in respect of data processing, a correction signal which merely reproduces a contrast value in a specific monitored sample volume, i.e. a specific reference section of the eye 2, is also possible as a motion signal, wherein this monitored section or reference section naturally lies at a fixed distance from the OCT 1. By fixed distance is meant a fixed optical wavelength as far as the detector 11 along the sample beam path 7 and the detection beam path 10.

In an embodiment, the control apparatus 3 uses the correction signal to correct the contrast signal. It is particularly preferred, because of the associated ease of computation and, simultaneously, high accuracy, that the control apparatus 3 corrects the measurement signal, thus the interference signal, of the detector 11 by means of the correction signal, before the contrast signal is generated by Fourier transform.

Figure 2:
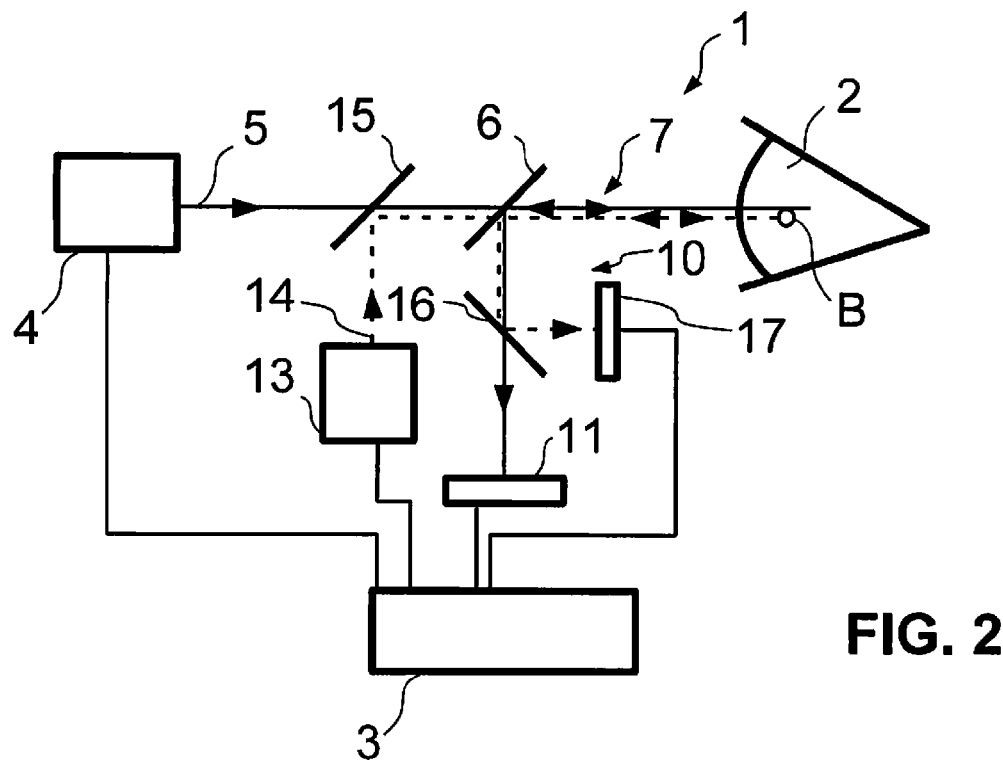
FIG. 2 is an OCT similar to that of FIG. 1a, but with a sample-motion detector that operates interferometrically.

FIG. 2 shows a variant in the implementation of the sample-motion detector 12 which also operates interferometrically. The structure of FIG. 2 is based on the structure of FIG. 1b, but is not to be understood as limiting. The sample-motion detector of FIG. 2 can of course also be used with the structure of FIG. 1a.

The sample-motion detector 12 comprises a correction laser 13 which emits correction radiation 14 which is superimposed on the measurement radiation 5 via a beam splitter 15. The correction radiation 14 differs from the measurement radiation 5 with the result that the superimposed radiations can later be separated from each other again. The polarization or the wavelength for example can serve as a distinguishing feature. The beam splitter 15 is then suitably formed as a polarizing splitter or as a dichroic beam splitter or combiner. The polarization-optical difference or separation and combination of measurement radiation 5 and correction radiation 14 is technically particularly advantageous, as dichroic beam splitters for closely neighbouring wavelengths are very expensive. Any influence of double refraction at the sample, for example at the anterior chamber of the eye 2 can be compensated for by suitable compensators.

The correction radiation 14 also strikes the eye 2, where it is reflected or scattered back and enters the detection beam path 10. Here, it is separated off by a further suitably formed beam splitter 14 from the measurement radiation 5 superimposed with it, which has also been reflected or scattered back from the eye, and reaches an independent detector 17. Correction radiation 14 interfering in itself thus falls onto this detector from areas of the eye 2 lying within the coherence length of the correction radiation 14. The detector 17 thus delivers an interferometric correction signal similar to the measurement signal 11. The central wavelength of the correction radiation is not tuned, with the result that there are interferences of radiation of a constant wavelength.

There is also the possibility of splitting the correction radiation into several portions which are focussed for example on different parts of the sample or adapted, in their polarization state, to the effect of the sample parts.

The spectral bandwidth of the correction radiation 14 corresponds to that of the measurement radiation. Laser types, which can also be used for the measurement laser 4, come into consideration as correction laser 13.

The control apparatus 3 thus receives from the detector 17 a correction signal which is also an interference signal and is of a similar type to the measurement signal from the detector 11. However, the central wavelength of the correction laser is not tuned, but remains fixed. The correction signal is thus a measure of the temporal changes in length in a reference area B within the sample 2 which is defined by the coherence wavelength of the correction radiation 14 and the wavelengths in the sample and detection beam path. The reference area B is, as already mentioned, spatially fixed vis-à-vis the OCT 1, thus shifts during movements of the eye 2 respectively in the eye 2. Thus, movements in the eye 2 or movements of the eye 2 result in a change in the correction signal, with the result that the correction signal can be used to correct the measurement signal by modifying the measurement signal in the opposite direction to the changes of the correction signal.

In detail, the reflexes of cornea front surface and fundus of the eye are coherently superimposed, both in the measurement and in the correction channel. The temporal phase change of the measurement signal (speed of phase change) essentially originates from the tuning of the source and is directly proportional to the speed of tuning and the eye length. If the eye length changes during the measurement, a further (ancillary) phase change results. In the correction signal the central wavelength of which is not tuned, the phase change is measured separately by the change in eye length and the measurement signal can thus be corrected, with the result that the average eye length can be calculated from the corrected signal. The correction calculation takes place as explained above in the general part of the description.

Figure 3:
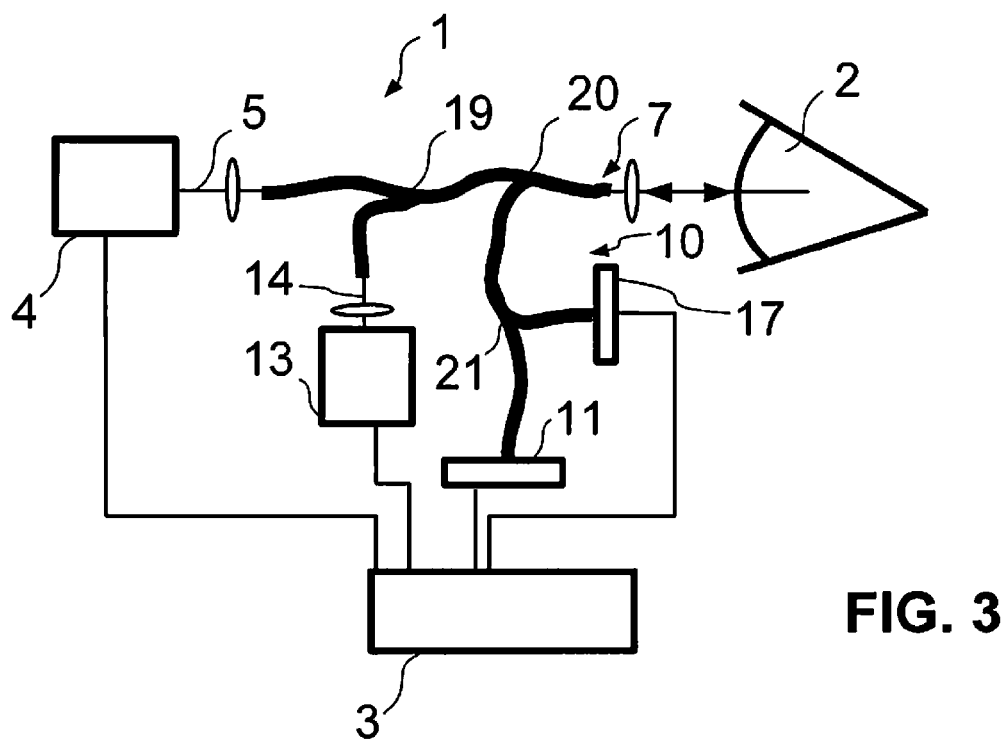
FIG. 3 is an OCT similar to FIG. 2, but with a fibre-optic structure.

FIG. 3 shows a structure of the OCT 1 of FIG. 2 based on fibre optics. Here, the beam splitter 15 is replaced by a fibre coupler 19, the beam splitter 6 by a fibre coupler 20 and the beam splitter 16 by a fibre coupler 21. Apart from this, the structure of FIG. 3 corresponds to that of FIG. 2.

In respect of the correction of the measurement signal, for all embodiments, the following development can be used which starts from the knowledge that a change in length or movement of the eye leads in the measurement signal as well as in the correction signal to a phase change due to the change in eye length and to a change in amplitude due to the shift, caused by the eye movement, of a reflection or backscattering point in the eye 2. It is therefore possible in a development to differentiate between phase change and change in amplitude.

A variant of this differentiation is a heterodyne detection in which the wavelength of both the measurement laser 4 and the correction laser 13 is altered around the central wavelength such that the measurement signal changes because of the interference of the reflexes from different depths of the eye 2 straight from a maximum to the closest minimum. It is advantageous if the measurement signal changes by at least twice the area in order to make the evaluation easier (then the area need not be determined so precisely). The amplitude function of the measurement signal or of the correction signal can then be produced from the difference of the two extremes and the phase function from the position of the two extremes relative to the controlled wavelength modulation.

Figure 4:
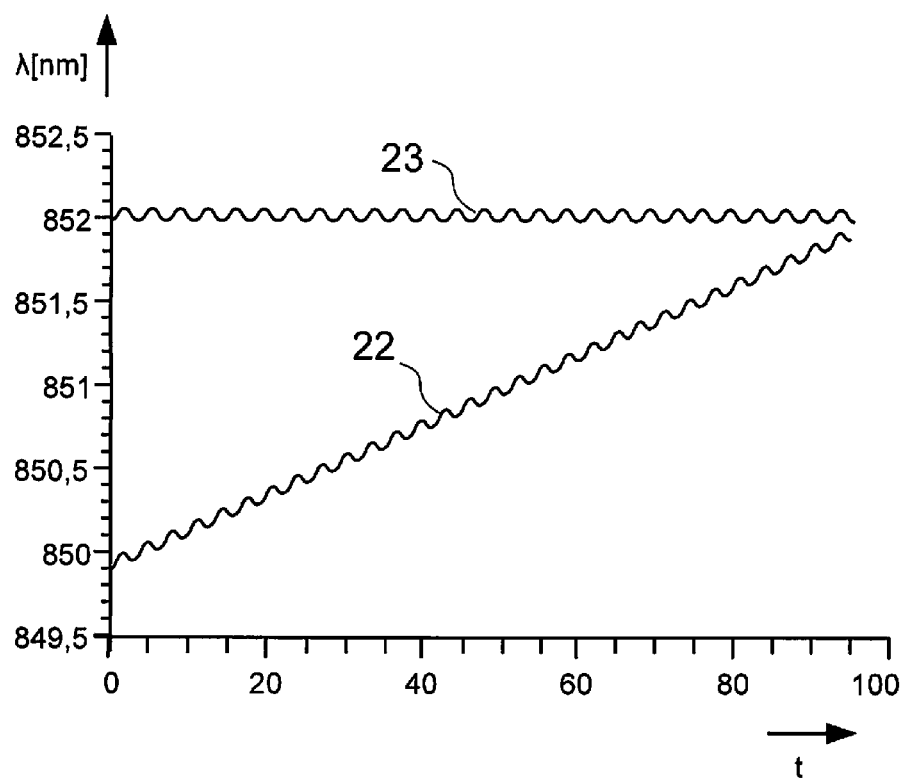
FIG. 4 is a graph which shows the wavelength course of the lasers of the OCT of FIG. 2 or 3, as results when tuning the central wavelength as well as within the framework of a heterodyne detection.

The course of the wavelengths is represented schematically in FIG. 4, which shows the wavelength (in nm) as a function of time t (in random units). The wavelength course 22 describes the measurement radiation 5 which is tuned from a value just below 850 nm to just below 852 nm, the course 23 describes the correction radiation 14. The central wavelength of the correction radiation 14 is continuously about 852 nm. Both wavelengths are modulated synchronously around the respective central wavelength, as the wavelength courses 22 and 23 in the representation of FIG. 4 show. For the purpose of illustration, FIG. 4 shows the modulation enlarged many times, as it would otherwise not be visible.

It is advantageous for the heterodyne technique which is used to split measurement signal and correction signal into phase function and amplitude function that the modulation of the measurement radiation 5 and of the correction radiation 14 can be effected by changing the supply current of the measurement laser 4 or of the correction laser 13 which can take place very quickly compared with any movement influences. The modulations around the central wavelengths are thus extremely high-frequency and therefore practically instantaneous compared with any movement influences. They are thus not distorted by movement influences.

All phase changes detected in this way in the correction signal originate in movement artefacts and are used to free the measurement signal of phase changes due to eye movement. For this, the phase function of the correction signal is removed from the phase function of the measurement signal in the control apparatus 3. Any changes in amplitude are undesirable, because of their origin in movement artefacts or any fluctuations in radiation intensity. The fluctuations in amplitude and the fluctuations in phase must therefore be separated. The evaluation then takes place as follows: the phase function of the signal wave $\Phi_S(t_i)$ and the phase function of the correction wave $\Phi k(t_j)$ as a function of time are known. Moreover, the change in frequency $\Delta F(t_i) = F(t_i) - F(t_{i-1})$ for discrete times ti is known. If the function $[\Phi_S(t_i) - \Phi k(t_i)]/\Delta F(t_1)$ is calculated and plotted against t, a straight line results the pitch of which is a measure of the eye length. In this case, the amplitude function and a Fourier transform are not needed.

The contrast signal, then free of eye movement influences despite the comparatively long tuning period of the wavelength of the measurement radiation 5, will now be generated by means of Fourier transform on the thus-corrected measurement signal.

As both phase function and amplitude function for the measurement signal are now available, mirror and autocorrelation artefacts can further be suppressed, whereby the measurement range achievable with the available tuning doubles.

An alternative to a heterodyne technique is quadrature component determination which also allows the splitting of the measurement signal and the correction signal into phase function and amplitude function, such as is known from the literature reference named at the beginning.

Finally, it is also an advantageous development to use the produced correction signal not only to correct the measurement signal but also at the same time to generate information on the eye movements, for example to carry out a pulse measurement.

A combination of the represented methods with a frequency clock is further possible. If the wavelength of the tuned source is altered e.g. by a sudden temperature change, the change in frequency as a function of time is not constant, but changes quickly at first and then slowly reaches a balance. In order to determine the represented function of the change in frequency $\Delta F(t_i) = F(t_i) - F(t_{i-1})$, a "frequency clock" which is state of the art is used. The radiation of the source passes through a plane plate of known thickness and refractive index. The beams which are reflected at the front and at the back of the plate are superimposed on a detector and the interference is measured. The speed of the phase change of this interference signal is a measure of the change in frequency.

The invention claimed is:

1. An SS-OCT interferometer apparatus for measuring a sample or an eye, the apparatus comprising:
    a measurement radiation source emitting measurement radiation that is adapted to interferometrically generate a measurement signal and to generate a depth-resolved contrast signal of the sample from the measurement signal by spectral tuning of a central wavelength of the measurement radiation;
    a control device;
    a sample-motion detector that provides a motion signal to the control device, the motion signal indicating movement of the sample or movement within the sample in the form of sample correction radiation;
    wherein before or during the generation of the depth-resolved contrast signal, the control device corrects the measurement signal with relation to measurement errors that are caused by movements of the sample or movements within the sample that occurred during the tuning of the central wavelength by utilizing the motion signal
    wherein the apparatus further comprises:
        a sample beam path, through which a part of the measurement radiation emitted from the measurement radiation source illuminates the sample;
        a detection beam path, which receives sample measurement radiation that is formed by the measurement radiation reflected or scattered back from the sample; and
        a detector device that detects the sample measurement radiation and provides a measurement signal; and
        wherein the sample-motion detector comprises a correction radiation source which emits correction radiation, and
        at least a part of the correction radiation is coupled into the sample beam path and illuminates the sample, and
            the detection beam path receives the sample correction radiation that is formed by the correction radiation reflected or scattered back from the sample in the form of the sample correction radiation and further comprising a correction radiation detector device adapted to detect the sample correction radiation separately from the sample measurement radiation, and
            the control device is adapted to generate a correction signal from the detection of the sample correction radiation by being adapted to remove a phase function of the correction signal from a phase function of the measurement signal.

2. The apparatus according to claim 1, wherein the motion signal indicates an optical contrast in a reference section which lies in the sample and at a fixed distance from the apparatus.

3. The apparatus according to claim 1, wherein the sample-motion detector detects the movement of a surface of the sample facing the interferometer apparatus selected from a group consisting of the corneal surface, a boundary surface in the sample, a boundary surface of the eye lens or a retina.

4. The apparatus according to claim 1, wherein a correction radiation source emitting correction radiation has a spectrally fixed central wavelength to interferometrically generate a correction signal indicating the position of a reference section.

5. The apparatus according to claim 1, wherein the correction radiation differs from the measurement radiation spectrally or in respect of polarization; and the detector device splits the sample correction radiation from the sample measurement radiation spectrally or in respect of the polarization, respectively.

6. The apparatus according to claim 1, wherein the control device is adapted to control modulations of the wavelength of the measurement radiation and of the correction radiation in each case around their central wavelength, and the control device is adapted to perform a heterodyne detection to determine the phase functions of the correction signal.

7. The apparatus according to claim 6, wherein, for the modulations, the control device modulates supply currents of the measurement and correction radiation sources.

8. The apparatus according to claim 7, wherein the control device modulates the supply currents with a stability of supply current generation better than 0.8µA.

9. The apparatus according to claim 7, wherein the control device determines an amplitude function of the measurement signal and rescales the amplitude function of the measurement signal such that there is a temporally constant amplitude, and generates the contrast signal by application of Fourier transform to the thus-corrected measurement signal.

10. The apparatus according to claim 1, wherein the detector device is adapted for a balanced detection of the sample measurement radiation and the sample correction radiation and the control device determines phase functions of the correction signal and of the measurement signal from results of the balanced detection and removes the phase function of the correction signal from the phase function of the measurement signal.

11. The apparatus according to claim 10, wherein the control device determines an amplitude function of the measurement signal and rescales the amplitude function of the measurement signal such that there is a temporally constant amplitude to create a corrected measurement signal, and generates the contrast signal by application of Fourier transform to the thus-corrected measurement signal.

12. The apparatus according to claim 1, wherein the apparatus comprises one of the following radiation sources providing the measurement radiation: an External Cavity Diode Laser, a Distributed Feedback Laser, a Distributed Bragg Reflector Laser, a Vertical Cavity Surface Emitting Laser and a Vertical External Cavity Emitting Laser.

13. The apparatus according to claim 1, wherein the apparatus comprises a radiation source providing the measurement radiation, the source having an operating temperature adjustment device for tuning the central wavelength, wherein the operating temperature adjustment device is controlled by the control device.

14. An SS-OCT method for measuring a sample, or an eye, comprising:
spectrally tuning a central wavelength of a measurement radiation;
generating a measurement signal utilizing interference;
generating a depth-resolved contrast signal of the sample from the measurement signal, detecting movements of the sample or in the sample and generating a motion correction signal indicating these movements;
correcting the measurement signal in respect of measurement errors which are caused by movements of the sample occurring during the tuning of the control wavelength, wherein the measurement signal is corrected by use of the correction signal and before or during the generation of the depth-resolved contrast signal,
wherein the method further comprises using correction radiation to generate the correction signal indicating the position of a reference section lying in the sample, the section having a fixed distance to the apparatus and correcting the measurement signal based on changes of the correction signal that occur during the tuning and removing a phase function of the correction signal from a phase function of the measurement signal.

15. The method according to claim 14, wherein the correction signal indicates an optical contrast in a reference section which lies in the sample and at a fixed distance from the apparatus.

16. The method according to claim 14, further comprising detecting a surface of the sample facing the apparatus or a boundary surface in the sample to detect the movements of the sample or in the sample.

17. The method according to claim 14, wherein the correction radiation is spectrally fixed in its central wavelength to interferometrically generate the correction signal.

18. The method according to claim 14,
illuminating the sample by a part of the measurement radiation thus forming the correction radiation;
detecting sample measurement radiation that is formed by the correction radiation reflected or scattered back from the sample to obtain a measurement signal, wherein a part of the correction radiation also illuminates the sample wherein the reflected or backscattered correction radiation constitutes sample correction radiation;
detecting sample correction radiation formed by correction radiation reflected or scattered back from the sample independently from the detection of the sample measurement radiation; and
generating the correction signal from the detected sample correction radiation.

19. The method according to claim 18, wherein the correction radiation differs from the measurement radiation spectrally or in respect of the polarization and further comprising splitting the reflected sample correction radiation from the sample measurement radiation spectrally or in respect of the polarization, respectively.

20. The method according to claim 18, further comprising
detecting the sample measurement radiation and the sample correction radiation in a balanced detection; and
determining the phase functions of the correction signal and of the measurement signal utilizing results of the balanced detection.

21. The method according to claim 20, further comprising rescaling an amplitude function of the measurement signal to comprise a temporally constant amplitude, and generating the contrast signal by calculating and utilizing a Fourier transform of the thus-corrected measurement signal.

22. The method according to claim 14, further comprising
modulating the wavelengths of the measurement radiation and of the correction radiation around their central wavelengths; and
determining the phase functions of the correction signal and of the measurement signal by a heterodyne detection.

23. The method according to claim 22, further comprising modulating supply currents of measurement and correction radiation sources providing the measurement and correction radiations.

24. The method according to claim 23, further comprising modulating the supply currents with a stability of supply current generation better than 0.8µA.

25. The method according to claim 23, further comprising rescaling an amplitude function of the measurement signal to comprise a temporally constant amplitude, and generating the contrast signal by calculating and utilizing a Fourier transform of the thus-corrected measurement signal.

26. The method according to claim 14, further comprising tuning a central wavelength of the measurement radiation via a variation in an operating temperature of a radiation source emitting the measurement radiation.

27. The method according to claim 14, further comprising correcting the measurement signal prior to generating an A-scan contrast signal.

\* \* \* \* \*

UNITED STATES PATENT AND TRADEMARK OFFICE
CERTIFICATE OF CORRECTION

PATENT NO. : 8,632,181 B2
APPLICATION NO. : 12/997804
DATED : January 21, 2014
INVENTOR(S) : Daniel Bublitz et al.

Page 1 of 1

It is certified that error appears in the above-identified patent and that said Letters Patent is hereby corrected as shown below:

On the Title Page

Under (75) Inventors: delete "Daniel Bublitz, Jena" and insert --Daniel Bublitz, Rausdorf--

In the Claims

Claim 14, Col. 13, line 51, delete "motion"

Signed and Sealed this
Seventh Day of October, 2014

Michelle K. Lee
*Deputy Director of the United States Patent and Trademark Office*